United States Patent [19]

Stedman

[11] 4,205,956
[45] Jun. 3, 1980

[54] NICKEL CARBONYL ANALYZER

[75] Inventor: Donald H. Stedman, Ann Arbor, Mich.

[73] Assignee: The International Nickel Company, Inc., New York, N.Y.

[21] Appl. No.: 40,844

[22] Filed: May 21, 1979

[51] Int. Cl.² .................... G01N 31/00; G01N 21/26
[52] U.S. Cl. ............................. 23/232 R; 23/232 E; 422/52; 250/361 C
[58] Field of Search .......... 422/52; 23/230 R, 232 R, 23/232 E, 230 PC; 250/361 C

[56] References Cited

U.S. PATENT DOCUMENTS

| 3,749,929 | 7/1973 | Wooten et al. | 422/52 X |
| 3,963,928 | 6/1976 | Zolner | 422/52 X |
| 3,973,914 | 8/1976 | Van Heusden | 422/52 |

Primary Examiner—R. E. Serwin
Attorney, Agent, or Firm—E. C. MacQueen; L. Messulam

[57] ABSTRACT

A sensitive portable detector for nickel carbonyl is provided which relies on chemiluminescence produced in the presence of ozone and carbon monoxide by pulse-modulating the carbon monoxide feed to the reactor chamber and detecting the resulting modulation of the output signal. The instrument is thus made insensitive to any NO which may be present in the gas sample.

12 Claims, 2 Drawing Figures

NICKEL CARBONYL ANALYZER

FIELD OF THE INVENTION

The present invention relates to a method and apparatus for detecting the presence of small amounts of nickel carbonyl or iron carbonyl in air samples.

BACKGROUND OF THE INVENTION

As has been known for many years, a unique way of producing nickel of high purity entails the formation and subsequent decomposition of nickel tetracarbonyl. While nickel refining by means of such a procedure has been practiced on a commercial scale, great care and elaborate safety measures are dictated by the well known toxicity of nickel carbonyl. Concern over the toxicity has led to regulations setting extremely low levels for the amount of nickel carbonyl which may be present in the atmosphere of an industrial plant. In one case a threshold value of 1 part per billion (ppb) by volume was as the maximum concentration of nickel carbonyl which may be present. Compliance with such stringent regulations has created a need for extremely sensitive detection equipment, capable of measuring such trace amounts in air samples taken from a workplace.

Various methods have been developed in the past for measuring small amounts of carbonyl gas. These include methods relying on chemical collection and analysis, plasma chromatography and infrared spectroscopy. None of these techniques has been able, however, to satisfy the needs for a piece of equipment which possesses not only sensitivity to minute levels and an acceptably fast response but also compactness to ensure its portability between locations in an industrial plant.

OBJECTS OF THE INVENTION

It is therefore an object of the present invention to provide an improved method and apparatus for detecting the presence of very small amounts of nickel carbonyl, $Ni(CO)_4$, or iron carbonyl, $Fe(CO)_5$, in an air sample.

It is a further object of the invention to provide such detection apparatus which is sufficiently compact to be portable.

Yet another object of the invention lies in ensuring that the apparatus and method provided are capable of accurate detection despite the presence of some nitric oxide in the air sample to be tested.

SUMMARY OF THE INVENTION

The invention is based on the chemiluminescence properties of carbonyls described by E. D. Morris and H. Niki in the Journal of the American Chemical Society, 92, 5471 (1970). A first instrument designed to detect nickel carbonyl by reliance on chemiluminescence in the presence of carbon monoxide and ozonized oxygen is described by the present inventor in Analytical Letters, 9, 81 (1976). While the instrument in question was found to be responsive to small quantities of nickel carbonyls, it nevertheless possessed various shortcomings. The more serious of these were:

(a) The size of the equipment and its power requirements rendered it essentially non-portable; and (b) strong interference was encountered between the chemiluminescence of nickel carbonyl to be detected and that resulting from any nitric oxide in the sample tested.

It has been found that these difficulties can be overcome with the aid of a chemiluminescence detection apparatus in which carbon monoxide is fed to a reactor as an intermittent stream.

Accordingly, the invention provides a method of measuring the concentration of nickel carbonyl or iron carbonyl in a gas comprising:

introducing the sample gas to be analyzed into a reactor as a first continuous stream;

introducing into the reactor an ozone-containing gas as a second continuous stream;

introducing into the reactor a carbon monoxide stream as an intermittent pulsating third stream;

detecting chemiluminescent light generated in the reactor and producing an electrical detection signal indicative thereof; and demodulating the detection signal to produce an output signal in response to the component of the detection signal which varies periodically with the same frequency as the pulsating third stream.

The method of the invention is embodied in a chemiluminescence detector for measuring the concentration of nickel carbonyl or iron carbonyl in a gas comprising:

a reaction chamber;

photodetection means responsive to light generated in the chamber to generate an electrical detection signal indicative thereof;

first means for feeding into the chamber a stream of sample gas to be analyzed;

second feed means for feeding into the chamber an ozone-containing gaseous stream;

third feed means which is electrically energizable and effective when energized to feed a carbon monoxide stream into the chamber;

flow-controlling means effective to supply a pulsed control signal to the third feed means, thereby periodically energizing the third feed means to cause an intermittent flow of carbon monoxide into the chamber; and demodulating means responsive to the detection signal to generate an output signal indicative of the component of the detection signal which varies periodically with the same frequency as the control signal.

A more detailed description of the now invention will now be given with reference to the accompanying drawings.

DETAILED DESCRIPTION OF THE EMBODIMENT

Figure 1:
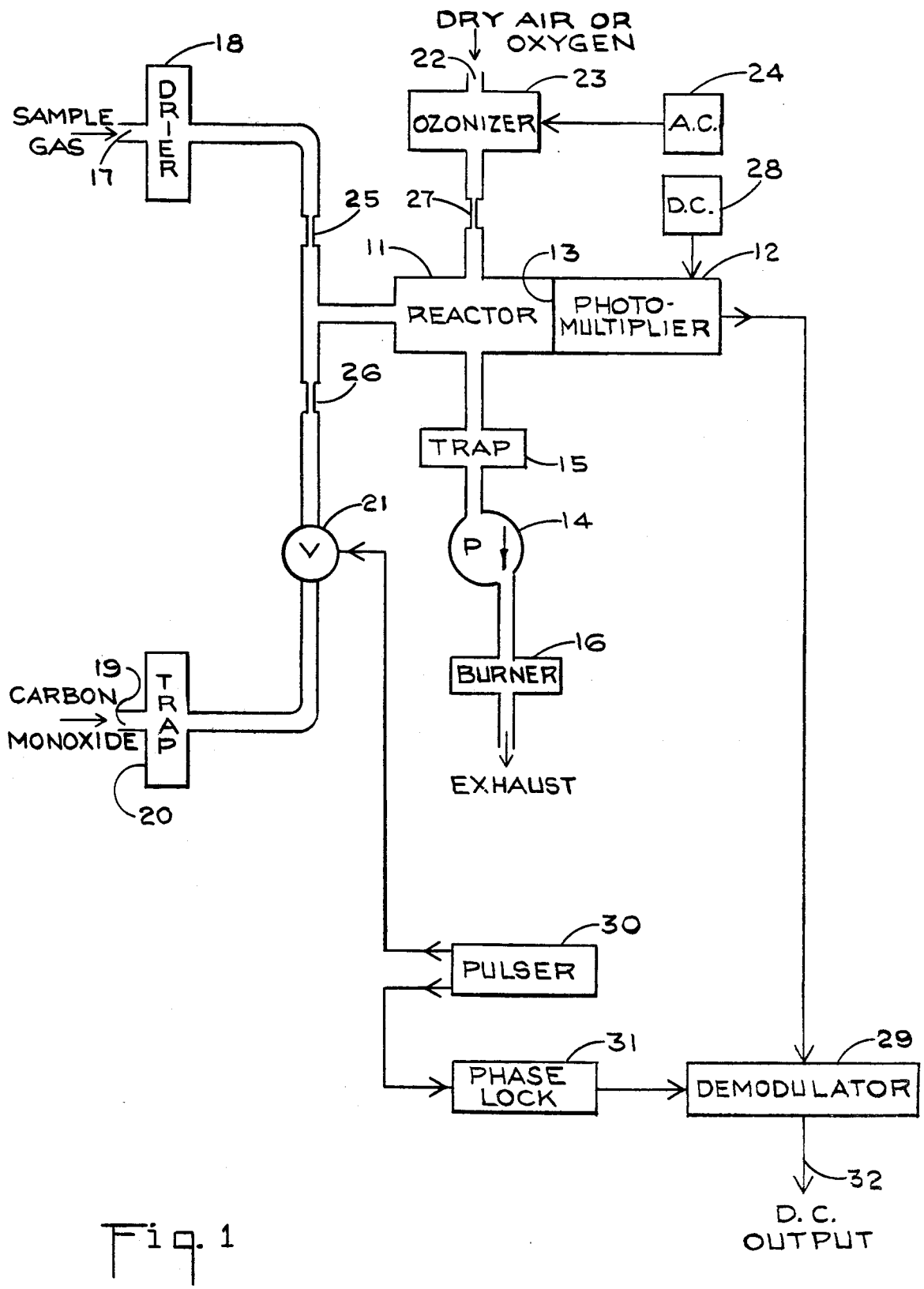
FIG. 1 is a block diagram depicting a carbonyl analyzer in accordance with the invention.

Referring to FIG. 1, apparatus is shown in which a sample gas, a carbon monoxide stream and an ozone-containing stream are mixed with one another within a reactor chamber 11 and the resulting luminescence in that chamber is detected by means of a photomultiplier tube 12 which is optically coupled to the chamber via a window 13. Flow of the gases into the chamber is induced by maintaining a reduced pressure within the chamber with the aid of an evacuation pump 14. The latter extracts the reacted mixture from the chamber 11 through an ozone trap 15, and exhausts it through a burner 16 which contains a precious metal catalyst to ensure that the exhaust vented into the plant atmosphere is essentially carbon monoxide-free.

The sample gas to be analyzed may show a wide variation in its moisture content. It has been found that water quenches the luminescence produced by nickel carbonyl, with the result that the sensitivity of the detector to nickel carbonyl would decrease with increasing sample humidity. For example, tests using various amounts of moisture content have shown that sensitivity can vary by a factor of four. Because the carbon monoxide stream and the ozone-containing stream have a moisture content which is both low and stable, the need for moisture control arises only with respect to the sample gas. For this purpose the sample gas sucked in at 17 is passed through a drier 18. We have used a commercially available permeation tube drier and found that without removing any carbonyl from the sample it reduced the moisture effect to such an extent that the instrument's sensitivity varied by only 5% or so for a range of sample gas extending from dry to water saturated.

A carbon monoxide supply is connected at 19 to communicate with the reactor chamber via a trap 20 and a valve 21. The trap 20 consists of gas scrubbing tube in which the carbon monoxide is first contacted with iodine crystals to remove any metal carbonyl traces that may be present therein and thereafter passes through some activated charcoal to remove any iodine vapor therefrom. The trap is necessitated by the fact that trace amounts of iron carbonyl may be present in the initial supply at levels of up to 0.7 parts per million (ppm), and the iodine/charcoal trap has proved a more consistent and effective method of purification than prior attempts at heating to decompose the carbonyl. Thus analysis of carbon monoxide exiting from the trap showed the carbonyl contamination to be less than 0.3 ppb. The valve 21 is a solenoid valve which was operated by applying to it pulses in the manner described hereinafter to cause a pulsating intermittent flow of carbon monoxide into the reaction chamber. The pulses which are supplied from an electronic oscillator should have a frequency of the order of 0.05–0.5 Hz with a 50% duty cycle, so that equal intervals of flow and no-flow are provided for the carbon monoxide stream.

A stream of dry air, or more preferably oxygen, is fed at 22 to an ozonizer 23. As is well known, the latter is a chamber containing an electrode to which a high voltage is applied from an AC supply 24. The ozonizer 23 is energized on a continuous basis so that in operation a feed of ozone/oxygen is delivered to the reaction chamber. As in the case of the carbon monoxide and the sample gas streams, this ozonized stream is sucked into the chamber 11 under the influence of the reduced pressure maintained therein.

The relative flow rates of the three gaseous streams fed into the reaction chamber are controlled by the head pressures available at the points 17, 19 and 28 respectively as well as by capillary constrictions 25, 26 and 27 respectively in the flow paths of the stream. The sample gas will generally be fed on demand at ambient pressure, while the head pressures of carbon monoxide and oxygen are adjusted by means of regulators on the gas supplies.

The photomultiplier tube 12 is optically coupled to the reactor chamber 11 via a window 13 which may, but need not, comprise a filter of predetermined band pass. The use of a filter is not required for differentiating between luminescence resulting from nickel carbonyl and that resulting from a noncarbonyl interferent. For this reason it is possible to make use of any transparent glass window 13. However, if it is desired to provide a better differentiation between nickel carbonyl and iron carbonyl, a colored filter may be used at 13 and in particular a green interference filter having a band pass of 10 nanometers (nm) centered at 492 nm has been found effective for such purpose. The photomultiplier tube requires a high voltage supplied by a stabilized DC source 28 and delivers a detection signal to a demodulator 29.

Modulation of the carbon monoxide feed stream is controlled by a pulser 30 which provides a control signal to energize the valve 21 periodically. The control signal emitted by the pulser 30 is also fed to phase locking circuit the function of which is to supply a reference signal to the demodulator 29, which reference signal comprises pulses having the same frequency as the pulses in the control signal, but delayed relative thereto to ensure a predetermined phase difference between the control and reference signals. The demodulator 29 operates in response to the reference signal as a tuned receiver for sensing components of the detection signal which vary periodically with the same frequency as the control signal and providing a DC output 32 indicative of those components.

Figure 2:
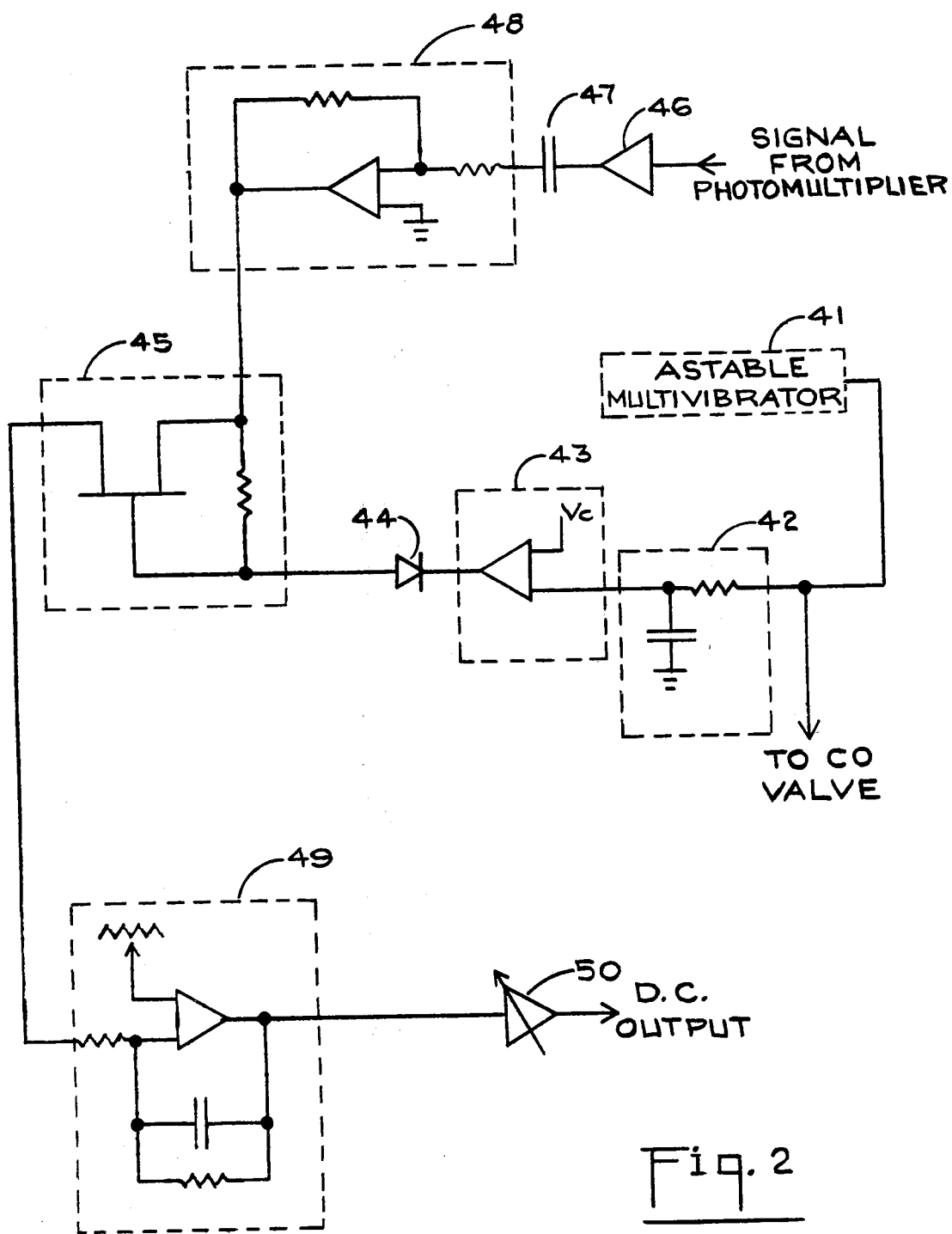
FIG. 2 is a schematic illustration of the electrical circuits used in the apparatus of FIG. 1.

Referring now to FIG. 2, the modulation and demodulation circuitry will now be described. The pulser used to modulate the carbon monoxide flow comprises an astable multivibrator 41. The signal from the latter is fed to the carbon monoxide valve 21 of FIG. 1 as well as to a delay network 42 which provides the desired phase shift. The output of the delay network is squared by means of an amplifier 43 functioning as a comparator between the delayed signal and a comparison voltage $V_C$. A diode 44 connects the squared output of the comparator, which output constitutes the reference signal for demodulation purposes, to the gate terminal of a field effect transistor which is operated in a switching mode as a synchronous demodulator 45.

The detection signal produced by the photomultiplier tube is first applied to a buffer amplifier 46 and then coupled via a capacitor 47 to an amplifier 48. The latter is a feedback amplifier to predetermined gain and applies an amplified signal to the source terminal of the field effect transistor of the demodulator 45. The drain terminal of that field effect transistor provides a periodic output signal resulting from the periodic conduction through the transistor effected by the reference signal applied to its gate terminal. This periodic output signal is applied to an amplifying network 49 which includes a feed-back amplifier having a variable voltage applied to one input thereof to enable adjustment of the zero setting, and a capacitor to integrate and smooth the output. The smoothed output from the amplifier 49 is then fed to a buffer amplifier 50 of variable gain to enable the effective range of the instrument to be selectively adjusted. The DC output of amplifier 50 constitutes the output signal of the instrument indicative of carbonyl concentration in the feed gas and can be monitored by means of a meter or preferably a recording chart.

The precise mechanism whereby nickel carbonyl produces chemiluminescence is not clearly understood but it is believed that it might entail oxidation of the carbonyl by the ozone to produce NiO which would then take part in a sequence such as:

$$NiO + CO \rightarrow Ni + CO_2$$

$$Ni + O_3 \rightarrow NiO^* + O_2$$

$$NiO^* \rightarrow NiO + photon$$

where NiO and NiO* denote the gaseous diatomic oxide in its ground and excited states respectively.

Where the concentration of carbonyl to be detected is very small, it is necessary to differentiate between portions of the photomultiplier detection signal attributable to the carbonyl and other components of that signal. These other components arise essentially from:

(a) noise which is characteristic of the photomultiplier tube itself; and (b) interference from other materials capable of exhibiting chemiluminescence, notably NO which may be present in the gas.

The noise from the photomultiplier tube is present regardless of gas flow and it is known that modulation can be used to eliminate its interference. Thus apparatus is marketed by the Thermo-Electron Corporation of Waltham, Mass., and described in their U.S. Pat. No. 3,856,473, comprising an analyzer for detecting $NO_x$ compounds in a gas. The $NO_x$ detector in question is similar in many respects to the carbonyl analyzer of the present invention and in fact the present invention was reduced to practice by modifying an analyzer manufactured by Thermo-Electron Corporation. The $NO_x$ analyzer available commercially requires two gas feeds: the sample stream and an ozone-containing stream. It embodies the principle of modulation by providing a periodic control signal to energize an ozonizer intermittently and thereafter detect the component of the photomultiplier output which varies with the frequency of energization of the ozonizer. In this way the $NO_x$ signal emitted only when ozone is present is distinguished from the background noise emitted even when the oxygen fed to the reactor is ozone-free.

In the analyzer of the invention the ozone is fed into the reactor continuously and the carbon monoxide feed is made intermittent. As a result the demodulation enables the sensing of only the luminescence which is dependent on the presence of carbon monoxide, i.e., the luminescence resulting from carbonyls of nickel or iron in the sample.

TESTS

A test rig was used to confirm the benefit of using a modulated carbon monoxide feed to the reactor. The apparatus in question comprised a reaction chamber in which the feed streams could be supplied in any of three alternative ways:

(A) all streams fed in continuously;

(B) intermittent ozone feed by pulsing the ozonizer;

(C) intermittent carbon monoxide feed by pulsing the solenoid valve in the carbon monoxide feed line.

For the purpose of comparison tests were carried out using each of two sample gas streams: a first stream containing 57 ppm NO and a second stream containing 57 ppm NO as well as 4 ppb $Ni(CO)_4$. A continuous flow of the sample gas stream at the rate of about 100 ml/min was maintained. The oxone containing gas was fed into reactor at a rate of about 12 ml/min, while carbon monoxide flow was about 50 ml/min when continuous flow was used and 100 ml/min for about 50% of the time when pulsed flow was used. In Table 1 below are shown the DC output derived from the photomultiplier tube in the type A tests, and the AC output derived from the photomultiplier tube in the type B and C tests.

TABLE 1

| Condition | A: Continuous Flows (amps. DC) | B: Pulsed Ozone (amps. AC) | C: Pulsed CO (amps. AC) |
|---|---|---|---|
| Instrument Off | $<10^{-13}$ | $<10^{-13}$ | $<10^{-13}$ |
| Instrument On | $1 \times 10^{-9}$ | $0.4 \times 10^{-9}$ | $<10^{-13}$ |
| Sample: 5 ppm NO | $57 \times 10^{-9}$ | $59 \times 10^{-9}$ | $<10^{-13}$ |
| Sample: 55 ppm NO & 4 ppb $Ni(CO)_4$ | $87 \times 10^{-9}$ | $92 \times 10^{-9}$ | $31 \times 10^{-9}$ |

The above mentioned tests, which clearly showed the effectiveness of pulsating the CO stream as a method of isolating the signal arising from nickel carbonyl, were obtained without the use of any optical filter between the photomultiplier tube and the reactor which was a 150 ml chamber.

Like nickel carbonyl, iron carbonyl exhibits the luminescence phenomenon only in the presence of carbon monoxide. The spectra of the light emitted by the oxides resulting from the two carbonyls differ from one another of course and it is possible to improve the specificity of the reactor to one or other of the species by using an appropriate filter or by using a photodetector which is sensitive to a specific waveband. Thus specificity to $Ni(CO)_4$ is greatly improved by using a green filter as opposed to the red filter customarily incorporated in a $NO_x$ detector. By way of illustration it can be stated that operation of the test apparatus using a first sample gas containing 1 ppb of $Ni(CO)_4$ and a second sample gas containing a similar concentration of $Fe(CO)_5$ using a red filter effective to pass wavelengths greater than 600 nm gave instrument readings of 68 and 14 nA respectively. Thus the relative sensitivity to nickel was a little better than 4 to 1. When the filter was replaced by a green filter which had a 10 nm bandpass centered at 492 nm, the resulting signals from the nickel- and iron-containing samples were respectively 69 and 0.25 nA, i.e., a relative sensitivity better than 250 to 1 for nickel over iron.

A series of tests was carried out using the apparatus of the invention illustrated in the drawings. The chamber in this apparatus had a volume of 150 ml. The ozonizer was supplied with dried room air. The unit was provided with a pump which produced an overall displacement of about 2.4 l/min but a by-pass loop enabled a lower flow to be maintained through the reaction chamber itself. By suitable manipulation of the bypass and choice of the capillary constrictions in the feed lines, the effect of different pressures in the reactor could be studied. It was found that it was unnecessary to resort to very low pressures and indeed the detector could be used effectively with reactor pressures as low as about 200 Pascals or as high as about 40,000 Pascals.

The effect of varying the relative flow rates of the gas streams was studied to determine optimum conditions. Using a 600 ml/min flow of a sample stream containing 74 ppb of $Ni(CO)_4$ and a pulsed CO feed of 400 ml/min (i.e., an average CO feed of 200 ml/min), it was found that a 70 ml/min flow of ozonized air gave optimum results.

Tests with a 70 ml/min ozone stream feed and a 200 ml/min average CO feed showed that there is no benefit in increasing the flow rate of the sample gas above 600 ml/min.

A relative increase in the carbon monoxide flow rate does produce improved instrument sensitivity as indicated by the results of Table 2 below. Here the instrument reading (as percentage of full scale) is shown for average carbon monoxide flow rates of 100-250 ml/min, the sample stream and ozone stream flow rates being 600 ml/min and 50 ml/min respectively in all cases.

TABLE 2

| Average CO flow ml/min | Instrument Reading (%) |
|---|---|
| 100 | 30 |
| 200 | 60 |
| 250 | 90 |

Of course, to avoid excessive use of CO, the higher flow rates should only be resorted to if the desired sensitivity necessitates their use.

The test data as a whole suggests the following choice of parameters:

(a) The sample gas is preferably fed at a rate of about 350 ml/min, (attained by applying a head pressure of 82 KPa to a capillary constriction of 3.8 cm length and 0.2 mm diameter).

(b) The ozonated air is preferably fed at a rate of about 70 ml/min (attained by applying a head pressure of 34 KPa to a capillary constriction of 3.8 cm length and 0.15 mm diameter).

(c) The carbon monoxide is preferably pulsed at a frequency of 0.5 Hertz (i.e., with a square wave giving 1 second of flow and 1 second of no flow) at an average rate of about 90 ml/min (attained with a head pressure 28 KPa applied to a capillary 3.8 cm long and 0.2 mm in diameter).

The NO rejection when operating under the preferred conditions was found to be excellent. For example, a 50 ppm NO content in the sample stream produces a signal of the same size as at 2 ppb nickel carbonyl contamination. Thus the rejection of NO over $Ni(CO)_4$ can be expressed as a 25,000 to 1 ratio.

The method of the invention has been shown to provide a carbonyl detector which is lightweight and portable, and which is relatively unaffected by large amounts of NO present in the gas analyzed. It is possible by making use of both the carbon monoxide modulation and a system of selectable optical filters to provide a single instrument capable of analyzing for $Ni(CO)_4$, $Fe(CO)_5$ or NO.

While the present invention has been described with reference to a preferred embodiment thereof, it will be understood that various modifications or additions may be made to the embodiment without departing from the scope of the invention, which is defined by the appended claims.

I claim:

1. A method of measuring the concentration of nickel carbonyl or iron carbonyl in a gas comprising:
   introducing the sample gas to be analyzed into a reactor as a first continuous stream;
   introducing into said reactor an ozone-containing gas as a second continuous stream;
   introducing into said reactor a carbon monoxide stream as an intermittent pulsating third stream;
   detecting chemiluminescent light generated in said reactor and producing an electrical detection signal indicative thereof; and
   demodulating said detection signal to produce an output signal in response to the component of said detection signal which varies periodically with the same frequency as said pulsating third stream.

2. A method in accordance with claim 1 wherein said first and second continuous streams and said intermittent stream are introduced into said reactor by maintaining a reduced pressure within said reactor.

3. A method in accordance with claim 1 wherein said second continuous stream comprises a stream of ozonized dry air.

4. A method in accordance with claim 1 wherein said second continuous stream comprises a stream of ozonized oxygen.

5. A chemiluminescence detector for measuring the concentration of nickel carbonyl or iron carbonyl in a gas comprising:
   a reaction chamber; 1
   photodetection means responsive to light generated in said chamber to generate an electrical detection signal indicative thereof;
   first feed means for feeding into said chamber a stream of sample gas to be analyzed;
   second feed means for feeding into said chamber an ozone-containing gaseous stream;
   third feed means which is electrically energizable and effective when energized to feed a carbon monoxide stream into said chamber;
   flow-controlling means effective to supply a pulsed control-signal to said third feed means, thereby periodically energizing said third feed means to cause an intermittent flow of carbon monoxide into said chamber; and
   demodulating means responsive to said detection signal to generate an output signal indicative of the component of said detection signal which varies periodically with the same frequency as said control signal.

6. A detector in accordance with claim 5 including an exhaust pump connected to said chamber and effective to maintain a reduced pressure therein.

7. A detector in accordance with claim 5 wherein said second feed means comprises a source of dry air and an ozonizer which in operation is continuously energized.

8. A detector in accordance with claim 5 wherein said second feed means comprises a source of substantially pure oxygen and an ozonizer which in operation is continuously energized.

9. A detector in accordance with claim 5 wherein said third feed means comprises a source of carbon monoxide, purification means for removing any metal carbonyl impurities present in said carbon monoxide and electrically energizable valve means effective when energized to permit flow from said purification means to said chamber.

10. A detector in accordance with claim 5 wherein said photodetection means includes a photomultiplier tube optically coupled to said chamber.

11. A detector in accordance with claim 5 wherein said flow controlling means includes a multivibrator which in operation ensures that said control signal supplied to said third feed means produces alternating energization and deenergization of said third feed means of substantially equal durations.

12. A detector in accordance with claim 11 wherein said demodulating means comprises phase locking means connected to said multivibrator and effective to generate a reference signal delayed with respect to said control signal, and a synchronous demodulator connected to receive said detection signal and said reference signal.

* * * * *